(12) United States Patent
Saltiel et al.

(10) Patent No.: US 9,365,581 B2
(45) Date of Patent: Jun. 14, 2016

(54) DEUTERATED AMLEXANOX

(71) Applicant: THE REGENTS OF THE UNIVERSITY OF MICHIGAN, Ann Arbor, MI (US)

(72) Inventors: Alan R. Saltiel, Ann Arbor, MI (US); Hollis D. Showalter, Ann Arbor, MI (US); Scott Larsen, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/888,591

(22) PCT Filed: May 2, 2014

(86) PCT No.: PCT/US2014/036644
§ 371 (c)(1),
(2) Date: Nov. 2, 2015

(87) PCT Pub. No.: WO2014/179734
PCT Pub. Date: Nov. 6, 2014

(65) Prior Publication Data
US 2016/0060271 A1 Mar. 3, 2016

Related U.S. Application Data

(60) Provisional application No. 61/818,753, filed on May 2, 2013.

(51) Int. Cl.
| | | |
|---|---|---|
| A61K 31/44 | (2006.01) |
| C07D 491/052 | (2006.01) |
| A61K 31/436 | (2006.01) |
| A61K 45/06 | (2006.01) |

(52) U.S. Cl.
CPC .......... *C07D 491/052* (2013.01); *A61K 31/436* (2013.01); *A61K 45/06* (2013.01)

(58) Field of Classification Search
CPC .................................................. A61K 31/436
USPC ........................................................ 514/291
See application file for complete search history.

(56) References Cited

U.S. PATENT DOCUMENTS

| | | | |
|---|---|---|---|
| 4,143,042 A | 3/1979 | Nohara |
| 4,728,509 A | 3/1988 | Shimizu et al. |
| 5,362,737 A | 11/1994 | Vora et al. |
| 8,299,084 B2 | 10/2012 | Rao et al. |
| 8,946,424 B2 * | 2/2015 | Saltiel ................ C07D 491/052 546/89 |
| 2003/0124178 A1 | 7/2003 | Haley |
| 2012/0125325 A1 | 5/2012 | Bannister et al. |

OTHER PUBLICATIONS

Reilly et al. Nature Medicine, 19(3), 313-323.*
Berge et al., "Pharmaceutical salts." J Pharm Sci. Jan. 1977; 66(1):1-19.
Handbook of Pharmaceutical Salts, Properties, and Use, Stahl and Wermuth ed. 2002.
Kuriki et al., "Antiallergic action of amoxanox (AA-673), its main metabolite M-I and tranilast" Yakuri to Chiryo (1973-2000), 13(11): 6435-46, Journal, 1985 (Abstract only).
Kurita et al., "Efficient and convenient heterogeneous palladium-catalyzed regioselective deuteration at the benzylic position." Chem. Eur. J. 2008; 14(2):664-73.
Nohara et a., "Studies on antianaphylactic agents. 5. Synthesis of 3-(1H-tetrazol-5-yl)chromones, a new series of antiallergic substances." J Med Chem. Jan. 1977; 20(1):141-5.
Nohara et al., "Studies on antianaphylactic agents. 7. Synthesis of antiallergic 5-oxo-5H-[1]benzopyrano[2,3-b] pyridines." J Med Chem. May 1985; 28(5):559-68.
Nohara et al., "Studies on antianaphylactic agents—I : A facile synthesis of 4-oxo-4H-1-benzopyran-3-carboxaldehydes by Vilsmeier reagents" Tetrahedron 1974, vol. 30(19):3553-3561.
Obach, "Mechanism of cytochrome P4503A4- and 2D6-catalyzed dehydrogenation of ezlopitant as probed with isotope effects using five deuterated analogs." Drug Metab Dispos. Dec. 2001;29(12):1599-607.
Remington's Pharmaceutical Sciences, Mack Publishing Co. (A.R. Gennaro et. al. eds.1985).
Ukawa et al., "Synthesis of the metabolites and degradation products of 2-amino-7-isopropyl-5-oxo-5H-[1]benzopyrano [2,3-b]pyridine-3-carboxylic acid (Amoxanox)." Chem Pharm Bull (Tokyo). Oct. 1985; 33(10):4432-7.
Waibel et al., "Bibenzyl- and stilbene-core compounds with non-polar linker atom substituents as selective ligands for estrogen receptor beta." Eur J Med Chem. Sep. 2009; 44(9):3412-24.

* cited by examiner

*Primary Examiner* — Nizal Chandrakumar
(74) *Attorney, Agent, or Firm* — Casimir Jones S.C.; Thomas Isenbarger; David Casimir

(57) ABSTRACT

Provided herein is technology relating to deuterated amiexanox and particularly, but not exclusively, to compositions comprising deuterated amiexanox, methods of producing deuterated amiexanox, and uses of deuterated amiexanox. Provided herein are deuteratecl amiexanox compounds for the treatment of obesity, insulin resistance, diabetes, and steatosis. In addition, the deuterated compounds are anti-inflammatory antiallergic immunomodulators. e.g., for the treatment of diseases associated with inflammation. The deuterium kinetic isotope effect associated with placing deuterium at the site of metabolic derivatization slows metabolic derivatization and thus increases the lifetime of the active drug in vivo.

9 Claims, 1 Drawing Sheet

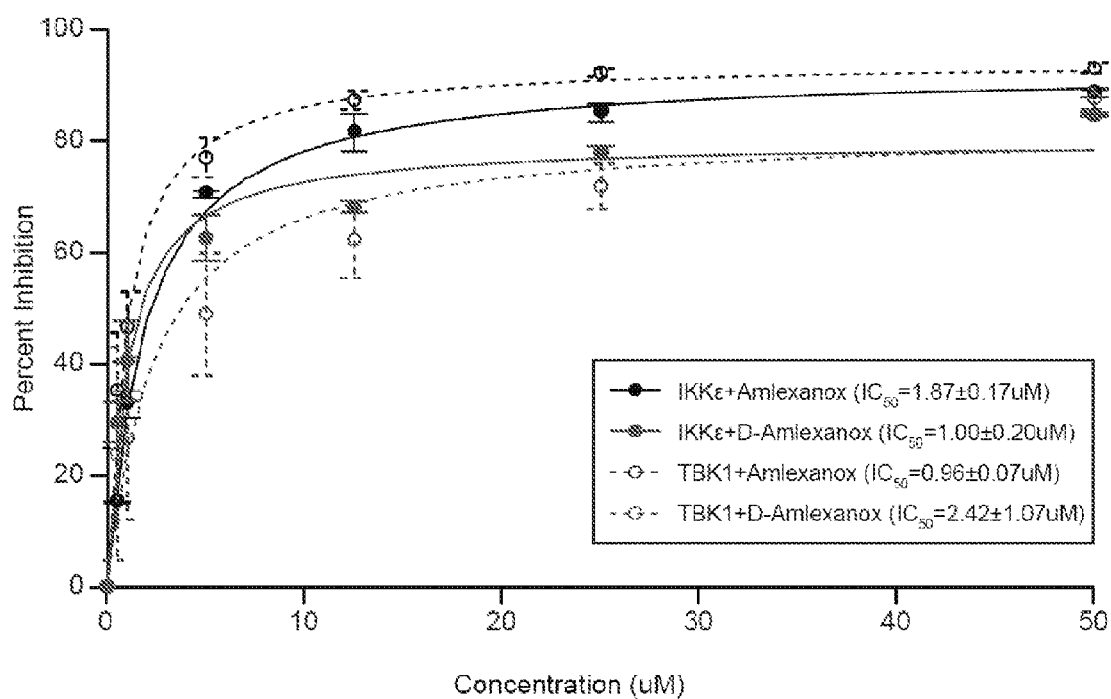

DEUTERATED AMLEXANOX

STATEMENT REGARDING FEDERALLY SPONSORED RESEARCH OR DEVELOPMENT

This invention was made with government support under DK060591 awarded by the National Institutes of Health. The government has certain rights in the invention.

This application is a 371 U.S. National Phase Entry of pending International Application No. PCT/US2014/036644, filed May 2, 2014, which claims priority to U.S. Pat. Appl. Ser. No. 61/818,753, filed May 2, 2013, each of which is incorporated herein by reference in its entirety.

FIELD OF INVENTION

Provided herein is technology relating to deuterated amlexanox and particularly, but not exclusively, to compositions comprising deuterated amlexanox, methods of producing deuterated amlexanox, and uses of deuterated amlexanox.

BACKGROUND

The incidence of the metabolic disorders of diabetes and obesity has reached epidemic levels. It has been estimated that over 120 million Americans are clinically over-weight and over 25 million have diabetes, including 1.9 million new cases in 2010 among those aged 20 and older. Obesity and diabetes can cause or contribute to the development of, or at least affect the treatment of, other diseases and disorders such as cardiovascular diseases, stroke, hypertension, kidney failure, asthma, and cancer. The economic burden of diabetes alone was estimated to be over $174 billion per year in 2007. Obesity and diabetes have a major impact on human health and the various national healthcare systems all over the world.

Recently launched weight-loss drugs have failed or have demonstrated limited efficacy and undesirable side effects. Similarly, despite a tremendous medical need, the pharmaceutical industry has realized only limited success developing therapeutics to manage diabetes. The most common therapeutics (sulfonylureas) are not effective and the most promising new drugs (thiazolidinediones) have demonstrated rare but fatal side effects. Thus, there is an urgent need for a more comprehensive understanding of the molecular basis of obesity and diabetes, for tests that allow early detection of predispositions to the disorders, and for more effective pharmaceuticals for preventing and treating these diseases and conditions.

SUMMARY

Accordingly, provided herein are deuterated amlexanox compounds for the treatment of obesity, insulin resistance, diabetes, and steatosis. In addition, the deuterated compounds are anti-inflammatory antiallergic immunomodulators, e.g., for the treatment of diseases associated with inflammation. The deuterium kinetic isotope effect associated with placing deuterium at the site of metabolic derivatization slows metabolic derivatization and thus increases the lifetime of the active drug in vivo. The deuterated amlexanox derivatives provided herein were demonstrated to have biological activity in inhibiting protein kinases (e.g., TBK1 or IKKε) associated with disease.

Accordingly, provided herein is technology related to a composition comprising deuterated amlexanox or a pharmaceutically acceptable salt thereof. In some embodiments, the composition comprising deuterated amlexanox or a pharmaceutically acceptable salt thereof further comprises non-deuterated amlexanox or a pharmaceutically acceptable salt thereof. Some embodiments provide a composition comprising a compound having a structure according to:

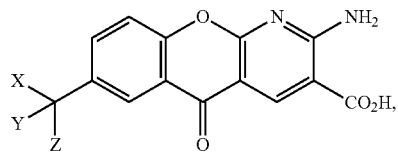

or a pharmaceutically acceptable salt thereof, wherein X, Y, or Z is a group that comprises deuterium (D). In some embodiments, X is a group that comprises D: in some embodiments, X and Y are groups that comprise D; and in some embodiments X, Y, and Z are groups that comprise D. In some embodiments, X, Y, or Z comprises or is $CD_3$; in some embodiments, X, Y, or Z comprises or is D: in some embodiments, X, Y, or Z comprises or is $CH_2CDH_2$: in some embodiments, X and Y comprise or are $CD_3$ and Z comprises or is D; in some embodiments, X and Y comprise or are $CH_3$ and Z comprises or is D; and in some embodiments, X comprises or is $CH_3$, Y comprises or is $CH_2D$, and Z comprises or is D.

Some embodiments provide a compound having the structural formula:

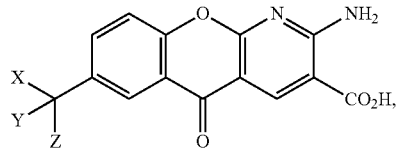

or a pharmaceutically acceptable salt thereof, wherein X, Y, or Z is enriched with deuterium more than 10%. In some embodiments, X, Y, or Z is enriched with deuterium more than 20%, 30%, 40%, 50%, 60%, 80%, 90%, 95%, 98%, or 99% or more.

In some embodiments are provided a composition comprising a compound or composition as described herein and a pharmaceutically acceptable carrier.

In some embodiments, the technology is related to use of a composition comprising a compound having a structure according to:

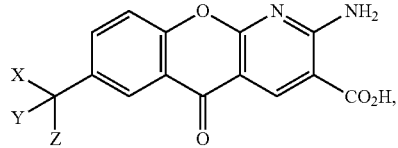

or a pharmaceutically acceptable salt thereof, for a medicament, wherein X, Y, or Z is a group that comprises D. Furthermore, in some embodiments, the technology provides use of a composition as provided herein and/or use of a compound as provided herein. Some embodiments provide use of a composition comprising a compound having a structure according to:

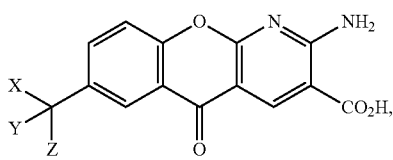

for a medicament to treat diabetes, insulin resistance, steatosis, hepatitis, obesity, allergic rhinitis, conjunctivitis, allergy, asthma, immune disorder, atherosclerosis, canker sore, ulcer, aphthous ulcer, symptoms of Behçet's Disease, or inflammation, wherein X, Y, or Z is a group that comprises D.

Some embodiments provide a method of treating a subject comprising administering to the subject a deuterated amlexanox. Some embodiments provide a method of treating a subject comprising administering to the subject a composition comprising a compound having a structure according to:

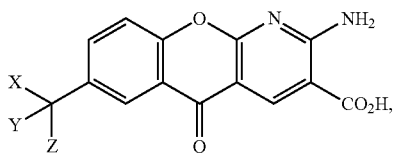

or a pharmaceutically acceptable salt thereof, wherein X, Y, or Z is a group that comprises D.

In some embodiments, the technology provides a method of treating a malady that is diabetes, insulin resistance, steatosis, hepatitis, obesity, allergic rhinitis, conjunctivitis, allergy, asthma, immune disorder, atherosclerosis, canker sore, ulcer, aphthous ulcer, symptoms of Behçet's Disease, or inflammation comprising identifying a subject in need of a treatment for the malady and administering to the subject a composition comprising a compound having a structure according to:

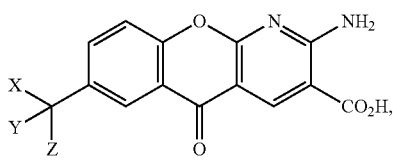

or a pharmaceutically acceptable salt thereof, wherein X, Y, or Z is a group that comprises D. In some embodiments, the technology provides a method of inhibiting a TBK1 or IKKε kinase in a patient comprising selecting a patient in need of a compound to inhibit a TBK1 or IKKε kinase and administering to the subject a composition comprising a compound having a structure according to:

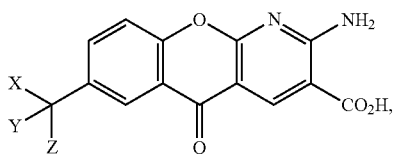

or a pharmaceutically acceptable salt thereof, wherein X, Y, or Z is a group that comprises D.

Some embodiments provide a method of manufacturing a deuterated amlexanox comprising providing a deuterated precursor and synthesizing the deuterated amlexanox from the deuterated precursor. In some embodiments the the deuterated precursor is a deuterated alcohol and in some embodiments the deuterated precursor is $R_2CDOH$.

Some embodiments provide a deuterated amlexanox produced by providing a deuterated precursor and synthesizing the deuterated amlexanox from the deuterated precursor. In some embodiments the the deuterated precursor is a deuterated alcohol and in some embodiments the deuterated precursor is $R_2CDOH$. Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 1 is a plot showing a dose-dependent inhibition of IKKε and TBK1 by embodiments of the compounds described herein.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein are new amlexanox compounds, pharmaceutical compositions made thereof, and methods to treat disease, e.g., by inhibiting kinase (e.g., IKKε or TBK1) activity, in a subject. The technology finds use in the treatment of disorders such as diabetes, insulin resistance, steatosis, hepatitis, obesity, allergic rhinitis, conjunctivitis, allergy, asthma, immune disorder, atherosclerosis, canker sore, ulcer (e.g., aphthous ulcer, symptoms of Behçet's Disease, etc.), or inflammation (e.g., inflammatory bowel disease, Crohn's disease, osteoarthritis, etc.).

In addition, the compounds find use to treat subjects affected with inflammatory diseases or disorders such as gout, arthritis (e.g., acute or chronic idiopathic inflammatory arthritis, osteoarthritis), psoriasis, chronic dermatosis, myositis, demyelinating diseases, chronic obstructive pulmonary disease (COPD), interstitial lung disease, glomerulonephritis, interstitial nephritis, chronic active hepatitis, Crohn's disease, inflammatory bowel disease, ulcerative colitis, plaque formation in atherosclerosis, degenerative diseases of the joints or nervous system, or multiple sclerosis (MS).

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the terms "subject" and "patient" refer to any animal, such as a mammal like a dog, cat, bird, livestock, and preferably a human (e.g., a human with a disease such as obesity, diabetes, or insulin resistance). Besides being useful for human treatment, certain compounds and formulations disclosed herein may also be useful for veterinary treatment of companion animals, exotic animals and farm animals, including mammals, rodents, and the like. More preferred animals include horses, dogs, and cats.

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "treating" includes reducing or alleviating at least one adverse effect or symptom of a disease or disorder through introducing in any way a therapeutic composition of the present technology into or onto the body of a subject. "Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

As used herein, "therapeutically effective dose" refers to an amount of a therapeutic agent sufficient to bring about a beneficial or desired clinical effect. Said dose can be administered in one or more administrations. However, the precise determination of what would be considered an effective dose may be based on factors individual to each patient, including, but not limited to, the patient's age, size, type or extent of disease, stage of the disease, route of administration, the type or extent of supplemental therapy used, ongoing disease process, and type of treatment desired (e.g., aggressive versus conventional treatment).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present technology.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium", when used to describe a given position in a molecule or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoralkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "aryl" refers to a carbocyclic aromatic ring or ring system. Unless otherwise specified, aryl groups are from 6 to 18 carbons. Examples of aryl groups include phenyl, naphthyl, biphenyl, fluorenyl, and indenyl groups.

As used herein, the term "heteroaryl" refers to an aromatic ring or ring system that contains at least one ring heteroatom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

As used herein, the term "heterocycle" refers to a non-aromatic ring or ring system that contains at least one ring heteroatom (e.g., O. S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms), and alkheteroaryl (where the alkyl group has from 1 to 4 carbon atoms).

As used herein, the term "alkoxy" refers to a chemical substituent of the formula —OR, where R is an alkyl group. By "aryloxy" is meant a chemical substituent of the formula —OR', where R' is an aryl group.

As used herein, the term "$C_{x-y}$ alkaryl" refers to a chemical substituent of formula —RR', where R is an alkyl group of x to y carbons and R' is an aryl group as defined elsewhere herein.

As used herein, the term "$C_{x-y}$ alkheteraryl" refers to a chemical substituent of formula RR", where R is an alkyl group of x to y carbons and R" is a heteroaryl group as defined elsewhere herein.

As used herein, the term "halide" or "halogen" or "halo" refers to bromine, chlorine, iodine, or fluorine.

As used herein, the term "non-vicinal O, S, or N" refers to an oxygen, sulfur, or nitrogen heteroatom substituent in a linkage, where the heteroatom substituent does not form a bond to a saturated carbon that is bonded to another heteroatom.

The compounds disclosed herein can exist as therapeutically acceptable salts. The term "pharmaceutically acceptable salt", as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to *Handbook of Pharmaceutical Salts, Properties, and Use*, Stah and Wermuth, Ed., (Wiley-VCH and VHCA, Zurich, 2002) and Berge et al. (1977) *J. Pharm. Sci* 66: 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, alpha-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide: and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

For structural representations where the chirality of a carbon has been left unspecified it is to be presumed by one skilled in the art that either chiral form of that stereocenter is possible.

Embodiments of the Technology
Deuterium Kinetic Isotope Effect

To eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C—C) n-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation given by $k=Ae^{-E_{act}/(RT)}$, which describes the dependence of the rate constant k for the chemical reaction on the absolute temperature T (in Kelvin), where A is the "pre-exponential factor", $E_{act}$ is the activation energy, and R is the universal gas constant. The Arrhenius equation states that, at a given temperature, the rate of a chemical reaction depends exponentially on the activation energy ($E_{act}$).

The transition state in a reaction is a short lived state along the reaction pathway during which the original bonds have stretched to their limit. By definition, the activation energy $E_{act}$ for a reaction is the energy required to reach the transition state of that reaction. Once the transition state is reached, the molecules can either revert to the original reactants or form new bonds giving rise to reaction products. A catalyst facilitates a reaction process by lowering the activation energy leading to a transition state. Enzymes are examples of biological catalysts.

Carbon-hydrogen bond strength is directly proportional to the absolute value of the ground-state vibrational energy of the bond. This vibrational energy depends on the mass of the atoms that form the bond and increases as the mass of one or both of the atoms making the bond increases. Since deuterium (D) has twice the mass of "regular" hydrogen, also called protium ($^1H$), a C-D bond is approximately 10 times stronger than the corresponding C—$^1H$ bond, making it more resistant to chemical or enzymatic cleavage. Consequently, if a C—$^1H$ bond is broken during a rate-determining step in a chemical reaction (e.g., the step with the highest transition state energy), then substituting a deuterium for that protium will cause a decrease in the reaction rate. This phenomenon is known as the deuterium kinetic isotope effect (DKIE). The magnitude of the DKIE can be expressed as the ratio between the rates of a given reaction in which a C—$^1H$ bond is broken and the same reaction where deuterium is substituted for protium. The DKIE can range from about 1 (no isotope effect) to very large numbers such as 50 or more. Substitution of tritium for hydrogen results in yet a stronger bond than deuterium and gives numerically larger isotope effects.

Deuterium ($^2H$ or D) is a stable and non-radioactive isotope of hydrogen that has approximately twice the mass of protium ($^1H$), the most common isotope of hydrogen. Deuterium oxide ($D_2$-O or "heavy water") looks and tastes like $H_2O$, but it has different physical properties.

Deuteration of pharmaceuticals to improve pharmacokinetics (PK), pharmacodynamics (PD), and toxicity profiles has been demonstrated previously with some classes of drugs. For example, the DKIE was used to decrease the hepatotoxicity of halothane, presumably by limiting the production of reactive species such as trifluoroacetyl chloride. However, this method is not applicable to all drug classes and thus the biological activity of a deuterated drug in vivo is not predictable. For example, deuterium incorporation can lead to metabolic switching and deuterium-protium exchange in vivo. Metabolic switching occurs when metabolism is hindered at one site and the resulting suppression of one metabolic pathway promotes metabolism at another site. Accordingly, metabolic switching can lead to different proportions of known metabolites as well as altogether new metabolites. This new metabolic profile may impart more or less toxicity. Deuterium-protium exchange within the physiological environment leads to loss of the deuterated form and thus minimizes the advantages of deuteration in vivo. Such problems are non-obvious and are not predictable a priori for any drug class.

In some embodiments deuterated amlexanox derivatives were synthesized and their biological activity tested. In particular, amlexanox is metabolized in humans by oxidation at the isopropyl group to produce the following compound (see. e.g., Kuriki et al. (1985) "Antiallergic action of amoxanox (AA-673), its main metabolite M-I and tranilast" *Yakuri to Chiryo* (1973-2000) 13(11): 6435-46):

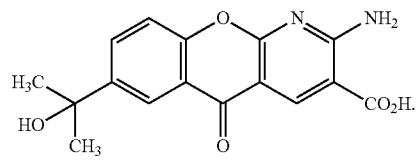 [SMILES: CC(C)(O)c1ccc2oc3nc(N)c(C(=O)O)cc3c(=O)c2c1]

The present technology was developed to inhibit metabolism at this site. Producing an amlexanox medicine with a longer half-life was contemplated to produce a compound having a greater efficacy and cost savings. In particular, the compounds provided herein are contemplated to reduce or eliminate unwanted metabolites, increase the half-life of the drug, decrease the number of doses needed to achieve a desired effect, decrease the amount of a dose needed to achieve a desired effect, increase the formation of active metabolites, decrease the production of deleterious metabolites in specific tissues, and/or create a more effective drug and/or a safer drug.

In some embodiments, certain compounds disclosed herein possess useful kinase inhibiting activity and may be used in the treatment or prophylaxis of a disorder in which a kinase plays an active role. Thus, certain embodiments also provide pharmaceutical compositions comprising one or more compounds disclosed herein together with a pharmaceutically acceptable carrier, as well as methods of making and using the compounds and compositions. Some embodiments provide methods for inhibiting a kinase activity. Other embodiments provide methods for treating a kinase-mediated disorder in a patient in need of such treatment, e.g., comprising administering to said patient a therapeutically effective amount of a compound or composition according to the present invention. Also provided is the use of certain compounds disclosed herein for use in the manufacture of a medicament for the prevention or treatment of a disorder ameliorated by inhibiting a kinase activity.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In some embodiments, the compound disclosed herein may expose a patient to $D_2O$ or DHO, e.g., about 0.000005% $D_2O$ or about 0.00001% DHO, assuming that all of the C-D bonds in the compounds as disclosed herein are metabolized and released as $D_2O$ or DHO.

In certain embodiments, the levels of $D_2O$ shown to cause toxicity in animals is much greater than even the maximum limit of exposure caused by administration of the deuterium compound as disclosed herein. Thus, in certain embodiments, the deuterium-compounds disclosed herein do not cause any additional toxicity due to the formation of $D_2O$ or DHO upon drug metabolism.

The deuterated compounds disclosed herein maintain the beneficial aspects of the corresponding non-isotopically enriched amlexanox molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Deuterated Amlexanox

The carbon-hydrogen bonds of amlexanox contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per 1018 protium atoms). The compounds provided herein have increased levels of deuterium at relevant sites of oxidation to thus produce a deuterium kinetic isotope effect that improves the pharmacokinetic, pharmacologic, and/or toxicologic profiles of amlexanox in comparison with amlexanox having naturally occurring levels of deuterium.

Accordingly, some embodiments provide a deuterated amlexanox, a derivative thereof, or a pharmaceutically acceptable salt thereof. Conventional amlexanox and its synthesis are described in U.S. Pat. No. 4,143,042, herein incorporated by reference in its entirety. Amlexanox (2-amino-7-isopropyl-1-azaxanthone-3-carboxylic acid: 2-amino-7-isopropyl-5-oxo-5H-chromeno[2,3-b]pyridine-3-carboxylic acid) has a CAS Number of 68302-57-8, a molecular weight of 298.3, and is synthesized as a crystalline solid.

However, no obvious and/or direct synthetic route is available to provide deuterated amlexanox using conventional amlexanox as a starting material. Thus, the technology described herein provides deuterated amlexanox and methods for producing deuterated amlexanox de novo using novel synthetic schemes to construct amlexanox from smaller deuterated compounds (see Examples).

In some embodiments, the compound has the structure of Formula I:

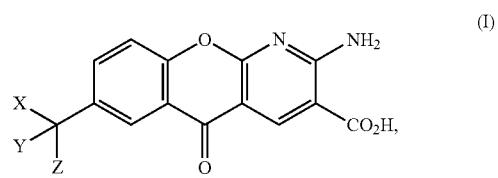

in which X, Y, or Z is a group that comprises a deuterium (D).

The compound of general Formula (I) can be converted to the corresponding organic amine salts, alkali metal salts, or ammonium salts by reacting (1) in the per se conventional manner with an organic amine (e.g., ethanolamine, diethanolamine, dl-methylephedrin, 1-(3,5-dihydroxyphenyl)-L-isopropylaminoethanol, isoproterenol, dextromethorphan, hetrazan (diethylcarbamazine), diethylamine, triethylamine, etc.), an alkali metal hydroxide (e.g., sodium hydroxide, potassium hydroxide, etc.) or ammonia, for example by mixing them together and heating in a suitable solvent.

Pharmacological Compositions

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. It is generally contemplated that the compounds according to the technology provided are formulated for administration to a mammal, and especially to a human with a condition that is responsive to the administration of such compounds. Therefore, where contemplated compounds are administered in a pharmacological composition, it is contemplated that the contemplated compounds are formulated in admixture with a pharmaceutically acceptable carrier. For example, contemplated compounds can be administered orally as pharmacologically acceptable salts, or intravenously in a physiological saline solution (e.g., buffered to a pH of about 7.2 to 7.5). Conventional buffers such as phosphates, bicarbonates, or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (e.g., salt formulation, esterification, etc.) that are well within the ordinary skill in the art. It is also well within the ordinary skill of the art to modify the route of administration and dosage regimen of a particular compound to manage the pharmacokinetics of the present compounds for maximum beneficial effect in a patient.

With respect to administration to a subject, it is contemplated that the compounds be administered in a pharmaceutically effective amount. One of ordinary skill recognizes that a pharmaceutically effective amount varies depending on the therapeutic agent used, the subject's age, condition, and sex, and on the extent of the disease in the subject. Generally, the dosage should not be so large as to cause adverse side effects, such as hyperviscosity syndromes, pulmonary edema, congestive heart failure, and the like. The dosage can also be adjusted by the individual physician or veterinarian to achieve the desired therapeutic goal.

As used herein, the actual amount encompassed by the term "pharmaceutically effective amount" will depend on the route of administration, the type of subject being treated, and the physical characteristics of the specific subject under consideration. These factors and their relationship to determining this amount are well known to skilled practitioners in the medical, veterinary, and other related arts. This amount and the method of administration can be tailored to achieve optimal efficacy but will depend on such factors as weight, diet, concurrent medication, and other factors that those skilled in the art will recognize.

In some embodiments, deuterated amlexanox, a derivative thereof, or a pharmaceutically acceptable salt thereof, is administered in a pharmaceutically effective amount. In some embodiments, deuterated amlexanox, a derivative thereof, or a pharmaceutically acceptable salt thereof, is administered in a therapeutically effective dose.

The dosage amount and frequency are selected to create an effective level of the compound without substantially harmful effects. When administered orally or intravenously, the dosage of deuterated amlexanox or related compounds will generally range from 0.001 to 10.000 mg/kg/day or dose (e.g., 0.01 to 1000 mg/kg/day or dose; 0.1 to 100 mg/kg/day or dose). In some exemplary embodiments, the deuterated amlexanox is administered in 1 or more 2-mg doses. In some exemplary embodiments, the deuterated amlexanox is administered as a 5% paste.

Methods of administering a pharmaceutically effective amount include, without limitation, administration in parenteral, oral, intraperitoneal, intranasal, topical, sublingual, rectal, and vaginal forms. Parenteral routes of administration include, for example, subcutaneous, intravenous, intramuscular, intrastemal injection, and infusion routes. In some embodiments, amlexanox, a derivative thereof, or a pharmaceutically acceptable salt thereof, is administered orally.

Pharmaceutical compositions preferably comprise one or more compounds of the present technology associated with one or more pharmaceutically acceptable carriers, diluents, or excipients. Pharmaceutically acceptable carriers are known in the art such as those described in, for example, *Remingtons Pharmaceutical Sciences*, Mack Publishing Co. (A. R. Gennaro edit. 1985), explicitly incorporated herein by reference for all purposes.

Amlexanox has been used as an oral tablet (e.g., 25-mg tablets) in Japan for treatment of bronchial asthma and as a topical oral paste in the United States (Aphthasol) for treatment of aphthous ulcers (canker sores). In some embodiments, deuterated amlexanox prepared similarly to either of these formulations may be used for the indications described herein. In other embodiments, different formulations are used. Aphthasol contains 5% amlexanox in an adhesive oral paste. Each gram of beige colored oral paste contains 50 mg of amlexanox in an adhesive oral paste base consisting of benzyl alcohol, gelatin, glyceryl monostearate, mineral oil, pectin, petrolatum, and sodium carboxymethylcellulose. Accordingly, the technology contemplates deuterated amlexanox provided in similar formulations.

In some embodiments, a single dose of deuterated amlexanox or a related compound is administered to a subject. In other embodiments, multiple doses are administered over two or more time points, separated by hours, days, weeks, etc. In some embodiments, compounds are administered over a long period of time (e.g., chronically), for example, for a period of months or years (e.g., 1, 2, 3, 4, 5, 6, 7, 8, 9, 10, 11, 12, or more months or years). In such embodiments, compounds may be taken on a regular scheduled basis (e.g., daily, weekly, etc.) for the duration of the extended period.

The present technology generally relates to therapeutic compositions and formulations comprising deuterated amlexanox. More particularly, the present technology relates to an oral medicament, a dietary supplement, a nutritional supplement, a food supplement, a food additive, a pharmaceutical, a nutraceutical, or nutratherapeutical formulation.

Combination Therapy

The compounds disclosed herein may also be combined or used in combination with other agents useful in the treatment of kinase-mediated disorders. Or, by way of example only, the therapeutic effectiveness of one of the compounds described herein may be enhanced by administration of an adjuvant (e.g., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In some embodiments, a compound provided herein is combined with an anti-obesity and/or an anti-diabetes therapy. For example, in some embodiments a compound described herein is provided with a meglitinide, e.g., to stimulate the release of insulin. Exemplary meglitinides are repaglinide (Prandin) and nateglinide (Starlix). In some embodiments, a compound described herein is provided with a sulfonylurea, e.g., to stimulate the release of insulin. Exemplary sulfonylureas are glipizide (Glucotrol), glimepiride (Amaryl), and glyburide (DiaBeta, Glynase). In some embodiments, a compound described herein is provided with a dipeptidyl peptidase-4 (DPP-4) inhibitor, e.g., to stimulate the release of insulin and/or to inhibit the release of glucose from the liver. Exemplary dipeptidyl peptidase-4 (DPP-4) inhibitors are saxagliptin (Onglyza), sitagliptin (Januvia), and linagliptin (Tradjenta). In some embodiments, a compound described herein is provided with a biguanide, e.g., to inhibit the release of glucose from the liver and/or to improve sensitivity to insulin. An exemplary biguanide is metformin (Fortamet, Glucophage). In some embodiments, a compound described herein is provided with a thiazolidinedione, e.g., to improve sensitivity to insulin and/or to inhibit the release of glucose from the liver. Exemplary thiazolidinediones include but are not limited to rosiglitazone (Avandia) and pioglitazone (Actos). In some embodiments a compound described herein is provided with an alpha-glucosidase inhibitor, e.g., to slow the breakdown of starches and some sugars. Exemplary alpha-glucosidase inhibitors include acarbose (Precose) and miglitol (Glyset). In some embodiments, a compound as described herein is provided with an injectable medication such as an amylin mimetic or an incretin memetic, e.g., to stimulate the release of insulin. An exemplary amylin mimetic is pramlintide (Symlin); exemplary incretin mimetics include exenatide (Byetta) and liraglutide (Victoza). In some embodiments a compound described herein is provided with insulin. The technology is not limited to any particular form of insulin, but encompasses providing the compounds described with any form of insulin. In some embodiments, the compounds described are used with an insulin injection. In some embodiments, a compound described herein is provided with more than one additional therapy (e.g., drug or other biologically active composition or compound), e.g., two, three, four or more compounds.

In certain embodiments, the compounds disclosed herein can be combined with one or more non-steroidal anti-inflammatory agents, anilide analgesics, glucocorticoids, and immunosuppressants.

In certain embodiments, the compounds disclosed herein can be combined with one or more non-steroidal anti-inflammatory agents, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoracoxib, faislamine, fenbuten, fenoprofen, flurbiprofen, ibuprofen, indometacin, ketoprofen, ketorolac, lornoxicam, loxoprofen, lumiracoxib, meloxicam, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinprazone, suprofen, tenoxicam, tiaprofenic acid, and tolmetin. In certain embodiments, the compounds disclosed herein can be combined with one or more anilide analgesics, including, but not limited to, acetaminophen and phenacetin.

In certain embodiments, the compounds disclosed herein can be combined with one or more glucocorticoids, including, but not limited to, beclometasone, budesonide, flunisolide, betamethasone, fluticasone, triamcinolone, mometasone, ciclesonide, hydrocortisone, cortisone acetate, prednisone, prednisolone, methylprednisolone, and dexamethasone.

In certain embodiments, the compounds disclosed herein can be combined with one or more immunosuppressants, including, but not limited to, fingolimod, cyclosporine A, azathioprine, dexamethasone, tacrolimus, sirolimus, pimecrolimus, mycophenolate salts, everolimus, basiliximab, daclizumab, anti-thymocyte globulin, anti-lymphocyte globulin, and CTLA4IgG.

In some embodiments, deuterated amlexanox, a derivative thereof, or a pharmaceutically acceptable salt thereof, is co-administered with one or more additional therapeutic agents or medical interventions. In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition.

The compounds disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids: endothelin converting enzyme (ECE) inhibitors, such as phosphoramidon; opioids, such as tramadol; thromboxane receptor antagonists, such as ifetroban; potassium channel openers; thrombin inhibitors, such as hirudin: hypothalamic phospholipids; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y(AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin): squalene synthetase inhibitors: fibrates; bile acid sequestrants, such as questran; niacin; anti-atherosclerotic agents, such as ACAT inhibitors; MTP Inhibitors: calcium channel blockers, such as amlodipine besylate; potassium channel activators; alpha-muscarinic agents; beta-muscarinic agents, such as carvedilol and metoprolol; antiarrhythmic agents; diuretics, such as chlorothlazide, hydroclorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase: farnesyl-protein transferase inhibitors: hormonal agents, such as estrogens/antiestrogens, androgens/antiandrogens, progestins, and luteinizing hormone-releasing hormone anatagonists, and octreotide acetate: microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; topoisomerase inhibitors; prenyl-protein transferase inhibitors; cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib: and miscellaneous agents such as, hydroxyurea, procarbazine, mitotane, hexamethylmelamine, gold compounds, platinum coordination complexes, such as cisplatin, satraplatin, and carboplatin.

Thus, some embodiments provide methods for treating kinase-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. Some embodiments provide therapeutic compositions comprising at least one compound disclosed herein in combination with one or more additional agents for the treatment of kinase-mediated disorders.

Kits

The technology provided herein also includes kits for use in the instant methods. Kits of the technology comprise one or more containers comprising deuterated amlexanox, a derivative thereof, or a pharmaceutically acceptable salt thereof, and/or a second agent, and in some variations further comprise instructions for use in accordance with any of the methods provided herein. The kit may further comprise a description of selecting an individual suitable treatment. Instructions supplied in the kits of the technology are typically written instructions on a label or package insert (e.g., a paper insert included with the kit), but machine-readable instructions (e.g., instructions carried on a magnetic or optical storage disk) are also contemplated. In some embodiments, the kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag, or a syringe. The containers can optionally include indicia indicating that the containers have been autoclaved or otherwise subjected to sterilization techniques. The kit can include instructions for administering the various solutions contained in the containers to subjects.

Methods of Treatment

The technology also relates to methods of treatment with deuterated amlexanox. According to another aspect of the technology, a method is provided for treating a subject in need of such treatment with an effective amount of deuterated amlexanox or a salt thereof. For example, some subjects in need of compositions according to the technology have diabetes, insulin resistance, steatosis, hepatitis, obesity, allergic rhinitis, conjunctivitis, allergy, asthma, immune disorder, atherosclerosis, canker sore, ulcer (e.g., aphthous ulcer, symptoms of Behçet's Disease, etc.), or inflammation (e.g., inflammatory bowel disease, Crohn's disease, osteoarthritis, etc.). The method involves administering to the subject an effective amount of deuterated amlexanox or salt thereof in any one of the pharmaceutical preparations described above, detailed herein, and/or set forth in the claims. The subject can be any subject in need of such treatment. In the foregoing description, the technology is in connection with deuterated amlexanox or salts thereof. Such salts include, but are not limited to, bromide salts, chloride salts, iodide salts, carbonate salts, and sulfate salts. It should be understood, however, that deuterated amlexanox is a member of a class of compounds and the technology is intended to embrace pharmaceutical preparations, methods, and kits containing related derivatives within this class. Another aspect of the technology then embraces the foregoing summary but read in each aspect as if any such derivative is substituted wherever "amlexanox" or "deuterated amlexanox" appears.

In some embodiments, provided herein are methods of treatment comprising: administering a pharmaceutically effective amount of deuterated amlexanox, a derivative thereof, or a pharmaceutically acceptable salt thereof, alone or in combination with another agent, to a subject having a condition in need of treatment. In some embodiments, the administration causes one or more of a reduction in or elimination of one or more symptoms of the condition, prevention of increased severity of one or more symptoms of the condition, and/or reduction, prevention, or elimination of further diseases or conditions.

In some embodiments, the methods provided comprise testing a subject for a disease or condition followed by administering deuterated amlexanox, a derivative thereof, or a pharmaceutically acceptable salt thereof, alone or in combination with other agents. In some embodiments, methods comprise administering to a subject deuterated amlexanox, a derivative thereof, or a pharmaceutically acceptable salt thereof, alone or in combination with other agents, followed by testing the subject for a disease or a condition. In some embodiments, methods comprise testing a subject for a disease or condition followed by administering deuterated amlexanox, a derivative thereof, or a pharmaceutically acceptable salt thereof, alone or in combination with other agents, followed by a second round of testing for a disease or condition (e.g., to monitor the effect of the treatment). In some embodiments, methods comprise testing a subject for a disease or condition followed by administering deuterated amlexanox, a derivative thereof, or a pharmaceutically acceptable salt thereof, alone or in combination with other agents, followed by a second round of testing for a disease or condition and a second administration of deuterated amlexanox, a derivative thereof, or a pharmaceutically acceptable salt thereof, alone or in combination with other agents, with this second administration being modified in dose, duration, frequency, or administration route in a manner dependent upon the results of the prior testing. In some embodiments, a subject is tested to assess the presence, the absence, or the level of a disease, e.g., by assaying or measuring a biomarker, a metabolite, a physical symptom, an indication, etc., to determine the risk of or the presence of the disease and thereafter the subject is treated with deuterated amlexanox based on the outcome of the test. In some embodiments, a patient is tested, treated, and then tested again to monitor the response to therapy. In some embodiments, cycles of testing and treatment may occur without limitation to the pattern of testing and treating (e.g., test/treat, test/treat/test, test/treat/test/treat, test/treat/test/treat/test, test/treat/treat/test/treat/treat, etc.), the periodicity, or the duration of the interval between each testing and treatment phase.

In some embodiments, the technology provided comprises use of deuterated amlexanox, a derivative thereof, or a pharmaceutically acceptable salt thereof, alone or in combination with other agents in the manufacture of a medicament for the treatment of a condition. In some embodiments, the technology provides deuterated amlexanox, a derivative thereof, or a pharmaceutically acceptable salt thereof, for the treatment of a condition.

Although the disclosure herein refers to certain illustrated embodiments, it is to be understood that these embodiments are presented by way of example and not by way of limitation.

EXAMPLES

Example 1

Synthesis of Deuterated Amlexanox

During the development of embodiments of the technology provided herein, experiments were performed to test synthetic schemes for producing deuterated amlexanox.

A. C-7 Mono- and Hepta-Deuterated Congeners.

Scheme A delineates a route to target compounds A-9a and A-9b. Commercially available 2-deuterio-2-propanol (A-1a) and 1,1,1,2,3,3,3-heptadeuterio-2-propanol (A-1b) are tosylated with tosyl chloride and pyridine (Obach (2001) "Mechanism of cytochrome P4503A4- and 2D6-catalyzed dehydrogenation of ezlopitant as probed with isotope effects using five deuterated analogs" *Drug Metab. Dispos.* 29(12): 1599-1607). The resulting tosylates A-2 are used to alkylate the Grignard reagent prepared from 1-bromo-4-methoxybenzene to provide the ethers A-3 (Obach, supra). Demethylation of the methyl ethers is effected with boron tribromide (Waibel et al. (2009) "Bibenzyl- and stilbene-core compounds with non-polar linker atom substituents as selective ligands for estrogen receptor beta" *Eur. J. Med. Chem.* 44(9): 3412-3424) to afford phenols A-4. Fries rearrangement of phenols A-4 with acetic anhydride and aluminum trichloride provides the acetylated phenols A-5 (Nohara et al. 1974 "Antianaphylactic agents. I. *Facile* synthesis of 4-oxo-4H-1-benzopyran-3-carboxaldehydes by Vilsmeier reagents" *Tetrahedron* 30(19): 3553-3561). Under Vilsmeier conditions, the phenols are cyclized to chromone aldehydes A-6 (Nohara 1974, supra). Conversion of the aldehydes to nitriles A-7 is effected with hydroxylamine and concentrated HCl (Nohara et al. (1977) "Studies on antianaphylactic agents. 5. Synthesis of 3-(1H-tetrazol-5-yl)chromones, a new series of antiallergic substances" *J. Med. Chem.* 20(1): 141-145). Cyclization to aminopyridine esters A-8 is accomplished by condensation with ethyl cyanoacetate and piperidine (Nohara et al. (1985) "Studies on antianaphylactic agents. 7. Synthesis of antiallergic 5-oxo-5H-[1]benzopyrano[2,3-b]pyridines" *J. Med. Chem.* 28(5): 559-568). Finally, deuterated amlexanox derivatives A-9a and A-9b are obtained by acidic hydrolysis of the ethyl esters (Nahara 1985, supra).

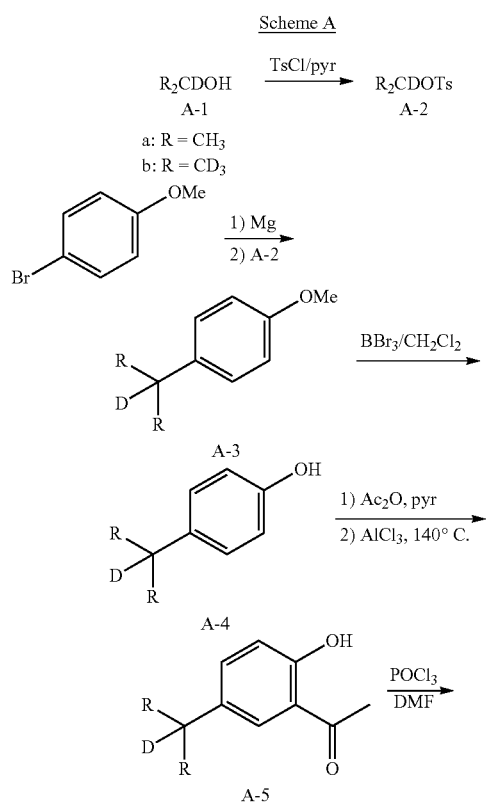

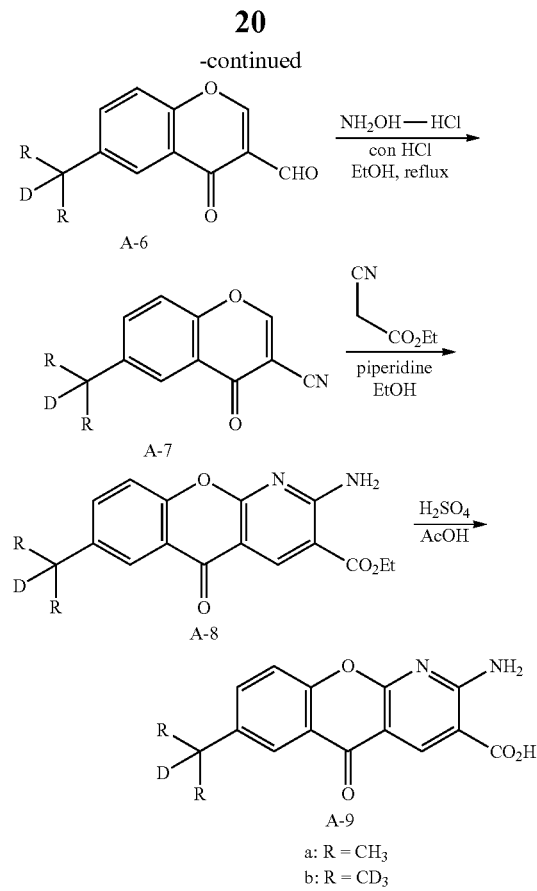

B. C-7 Dideutero Congener.

The synthesis of target compound B-4 is given in Scheme B. Compound B-1 was generated in a manner according to Ukawa et al. (1985) "Synthesis of the metabolites and degradation products of 2-amino-7-isopropyl-5-oxo-5H-[1]benzopyrano[2,3-b]pyridine-3-carboxylic acid (amoxanox)" *Chem. Pharm. Bull.* 33(10): 4432-7. Boc protection was carried out under standard conditions to give B-2, which was then treated with Wilkinson's catalyst and deuterium gas to provide dideutero product B-3. A two-stage deprotection sequence (eg, sodium hydroxide to hydrolyze the ester and hydrochloric acid to cleave the Boc carbamate) provided the targeted D2-amlexanox (B-4).

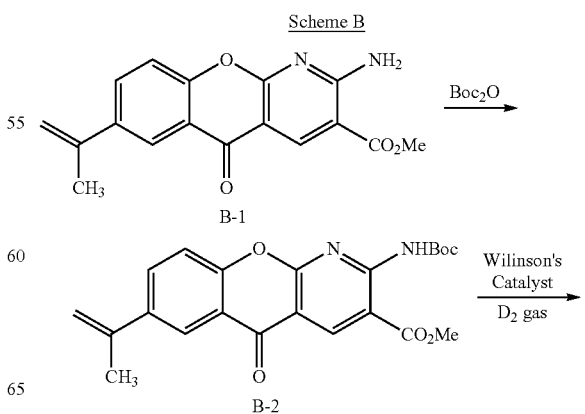

-continued

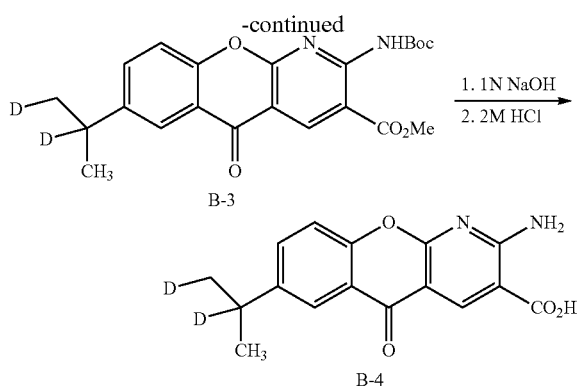

B-3

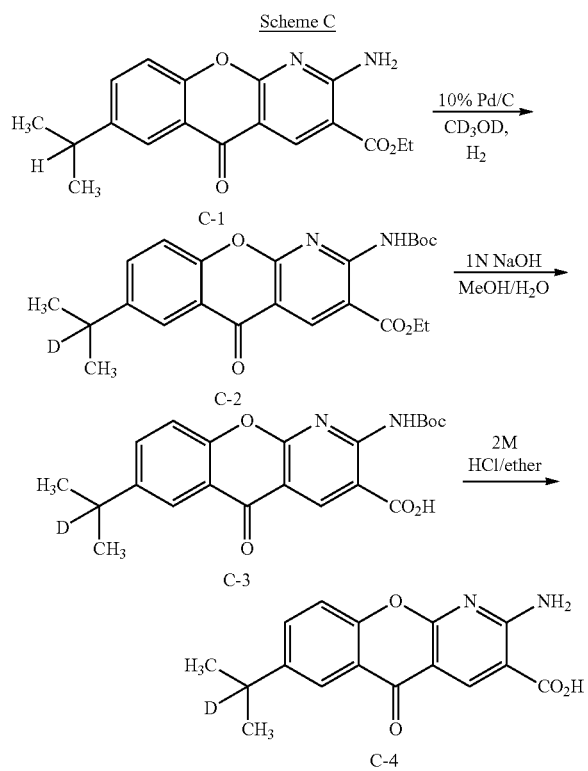

C. Alternate Scheme to C-7 Monodeutero Congener.

Compound C-1 is prepared in a manner similar to methyl 2-((tert-butoxycarbonyl)amino)-5-oxo-7-(prop-1-en-2-yl)-5H-chromeno[2,3-b]pyridine-3-carboxylate (B-1) from methyl 2-amino-7-isopropyl-5-oxo-5H-chromeno[2,3-b]pyridine-3-carboxylate (Nohara 1985, supra) and di-tert-butyl dicarbonate. The deuterium exchange is performed in a similar manner described in the literature (Kurita et al. (2008) "Efficient and convenient heterogeneous palladium-catalyzed regioselective deuteration at the benzylic position" *Chem. Eur. J.* 14(2): 664-673) to provide C-2. Deprotection is afforded by treatment of C-2 sequentially with aqueous sodium hydroxide with methanol as a co-solvent followed by treatment of C-3 with 2M HCl in dioxane to obtain C-4.

D. Experimental Procedures

Chemical names follow CAS nomenclature. Starting materials were purchased from Fisher, Sigma-Aldrich Lancaster, Fluka, or TCI-America and were used without purification. All reaction solvents were purchased from Fisher and used as received. Reactions were monitored by TLC using pre-coated silica gel 60 F254 plates. Silica gel chromatography was performed with silica gel (220 to 240 mesh) obtained from Silicycle. NMR spectra were recorded on a Varian 400 MHz spectrometer. Chemical shifts are reported in δ (parts per million), by reference to the hydrogenated residues of a deuterated solvent as an internal standard CDCl$_3$: δ=7.28 ($^1$H NMR). Mass spectra were recorded on a Micromass LCT time-of-flight instrument utilizing the electrospray ionization mode. Melting points were measured on a MEL-TEMP melting point apparatus and are uncorrected. The purity of the compounds was assessed via analytical rpHPLC with a gradient of 90% A:B to 10% A:B over 6 minutes (solvent A, H$_2$O: solvent B, acetonitrile; C18 column, 3.5 μm, 4.6×100 mm; 254 nm wavelength detection).

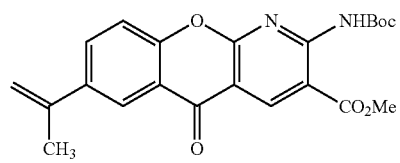 [SMILES: C=C(C)c1ccc2oc3nc(NC(=O)OC(C)(C)C)c(C(=O)OC)cc3c(=O)c2c1]

Methyl 2-((tert-butoxycarbonyl)amino)-5-oxo-7-(prop-1-en-2-yl)-5H-chromeno[2,3-b]pyrtdlne-3-carboxylate (B-2)

To a solution of methyl 2-amino-5-oxo-7-(prop-en-2-yl)-5H-chromeno[2,3-b]pyridine-3-carboxylate (0.044 g, 0.14 mmol) in dry THF was added di-tert-butyl dicarbonate (0.036 ml, 0.16 mmol) followed by N,N-diisopropylethylamine (0.028 nil, 0.16 mmol) and catalytic 4-dimethylaminopyridine. The resulting mixture was stirred overnight at room temperature and then diluted with ethyl acetate/ether, washed twice with saturated aqueous NaCl, and dried over MgSO$_4$. Purification by flash chromatography, eluting with 30% ethyl acetate/hexane, gave B-2 (0.04 g, 68.7%) as a white solid. HPLC (tR=9.14 minutes). NMR (400 MHz, CDCls) δ 9.34 (s, 1H), 8.35 (s, 1H), 7.94 (d, 1H), 7.58 (d, 1H), 5.51 (s, 1H), 5.23 (s, 1H), 3.95 (s, 3H), 2.24 (s, 3H), 1.41 (s, 9H).

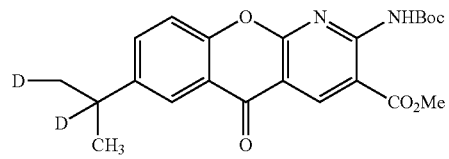 [SMILES: [2H]CC([2H])(C)c1ccc2oc3nc(NC(=O)OC(C)(C)C)c(C(=O)OC)cc3c(=O)c2c1]

Methyl 2-((tert-butoxycarbonyl)amino)-7-(D)-isopropyl-5-oxo-5H-chromeno[2,3-b]pyridine-3-carboxylate (B-3)

Wilkinson's catalyst (chlorotris(triphenylphosphine) rhodium(I): 0.04 g, 0.043 mmol) was dissolved in methyl ethyl ketone (10 ml) and deuterium gas was bubbled into the solution via a balloon and needle. A balloon of deuterium gas was attached to the reaction vessel and the mixture was stirred 1 hour before adding methyl 2-((tert-butoxycarbonyl)amino)-5-oxo-7-(prop-1-en-2-yl-5H-chromeno[2,3-b]pyridine-3-carboxylate (B-2; 0.04 g, 0.097 mmol) in methyl ethyl ketone (8 ml). The resulting mixture was stirred for 1 hour at room temperature, concentrated, and filtered through a plug of silica gel and eluting with 30% ethyl acetate/hexane. Concentration of the filtrate provided B-3 (0.035 g, 87%). HPLC (tR=9.27 minutes). NMR (400 MHz, CDCl$_3$) δ 9.34 (s, 1H), 8.16 (s, 1H), 7.68 (d, 1H), 7.55 (d, 1H), 3.95 (s, 3H), 1.40 (s, 9H), 1.31 (s, 3H), 1.29 (s, 2H).

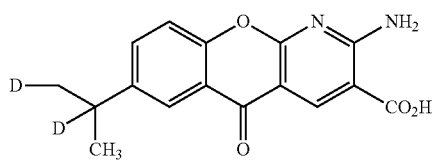 [SMILES: [2H]CC([2H])(C)c1ccc2oc3nc(N)c(C(=O)O)cc3c(=O)c2c1]

2-Amino-7-(D)-isopropyl-5-oxo-5H-chromeno[2,3-b]pyridine-3-carboxylic acid (B-4)

To methyl 2-((tert-butoxycarbonyl)amino)-7-(D$_2$)-isopropyl-5-oxo-5H-chromeno[2,3-b]pyridine-3-carboxylate (B-3; 0.03 g, 0.07 mmol) dissolved in methanol (5 ml) was added aqueous 1 M sodium hydroxide (0.14 ml, 0.14 mmol). The resulting mixture was stirred overnight at room temperature and then concentrated. The residue was dissolved in ethyl acetate (5 ml) and treated with excess 2-M HCl in dioxane (5 ml). After stirring for 2 hours, the mixture was concentrated to a residue that was triturated in methanol. The solids were collected and dried under vacuum at room temperature to give B-4 (0.012 g, 55.2%). HPLC (tR=6.48 minutes). NMR (400 MHz, CDCLh) δ 8.88 (s, 1H), 8.24 (br s, 1H), 7.90 (s, 1H), 7.65 (br s, 1H), 7.51 (d, 1H), 7.32 (d, 1H), 1.20 (s, 3H), 1.19 (s, 2H). ESI+MS m/z300.306 (M+H$^+$).

Example 2

Biological Activity of Deuterated Amlexanox

During the development of embodiments of the technology provided herein, experiments were conducted to test in vitro the biological activity of deuterated amlexanox. In particular, data were collected to quantify the inhibitory activity of a deuterated amlexanox toward the protein kinases IKKε and TBK1.

The effects of the compounds on these kinases were assayed in vitro. In vitro kinase assays were performed by incubating purified kinase (IKKε or TBK1) in kinase buffer containing 25 mM Tris (pH 7.5), 10 mM MgCl$_2$, 1 mM DTT, and 1 mM ATP for 30 minutes at 30° C. in the presence of 0.5 µCi γ-[$^{32}$P]-ATP and 1 µg myelin basic protein (MBP) per sample as a substrate. Kinase inhibitors were added at 50 µM and serially diluted (final concentrations are indicated). Kinase reactions were stopped by adding 4× sodium dodecyl sulfate (SDS) sample buffer and boiling for 5 minutes at 95° C. Supernatants were resolved by SDS-polyacrylamide gel electrophoresis, transferred to nitrocellulose, and analyzed by autoradiography using a Typhoon 9410 phosphorimager (GE Lifesciences, Piscataway, N.J.). The bands were quantified using ImageQuant.

Amlexanox and deuterated (D)-amlexanox inhibited the activities of both protein kinases, with IC50 values in the range of 1 to 2 µM. Dose-response data for IKKε are shown in Table 1. The results show that deuterated amlexanox inhibits IKKε and TBK1 in a dose-dependent manner (FIG. 1).

TABLE 1

| | Inhibition of IKKε | | | | | | |
|---|---|---|---|---|---|---|---|
| | Experiment 1 | | | Experiment 2 | | | Average |
| D-Amlexanox concentration | MBP-IKKε | Normalized $^{32}$P | % inhibition | MBP-IKKε | Normalized $^{32}$P | % inhibition | % inhibition |
| 50.0 µM | 1374.96 | 0.283097 | 71.69 | 1379.67 | 0.307902 | 69.21 | 70.45 |
| 25.0 µM | 1720.79 | 0.354301 | 64.57 | 2017.15 | 0.450196 | 54.99 | 59.78 |
| 12.5 µM | 2292.47 | 0.472007 | 52.80 | 2636.59 | 0.588444 | 41.16 | 46.98 |
| 5.0 µM | 2136.30 | 0.439852 | 56.01 | 2761.66 | 0.616358 | 38.36 | 47.19 |
| 1.0 µM | 3879.37 | 0.798741 | 20.13 | 4375.20 | 0.976473 | 2.35 | 11.24 |
| 0.5 µM | 4420.64 | 0.910186 | 8.98 | 4289.95 | 0.957448 | 4.26 | 6.625 |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the art are intended to be within the scope of the following claims.

We claim:

1. A method of treating a subject comprising administering to the subject a composition comprising a compound having a structure according to:

or more of X, Y, or Z is enriched with deuterium more than 1% an atom that is deuterium (D) and
a) X, Y, or Z is CD$_3$, D, or CH$_2$CDH$_2$;
b) X and Y are CD$_3$ and Z is D;
c) X and Y are CH$_3$ and Z is D; or
d) X is CH$_3$, Y is CH$_2$D, and Z is D wherein the subject has as malady that is diabetes. insulin resistance, steatosis, hepatitis, obesity, allergic rhinitis, conjunctivitis, asthma, canker sore and aphthous ulcer.

2. The method of claim 1 further comprising selecting a subject in need of inhibiting a TBK1 or a IKKε kinase.

3. The method of claim 1 further comprising testing the subject for a symptom of the malady.

4. The method of claim 3 further comprising a second administering of the compound to the subject based on a result of the testing.

5. The method of claim 2 further comprising testing the subject for an activity of the TBK1 or a IKKε kinase.

6. The method of claim 2 further comprising administering to the subject a second agent for treatment of a kinase-related disorder, for treatment of diabetes, and/or for treatment of obesity.

7. The method of claim 1 wherein the composition is a pharmaceutical composition.

8. The method of claim 3 wherein the testing comprises assaying or measuring a biomarker, a metabolite, a physical symptom, or an indication to determine the risk of or the presence of the disease.

9. The method of claim 7 wherein the pharmaceutical composition is administered to the subject in a dose that provides a concentration in a tissue of the subject that is inhibitory to a TBK1 or a IKKε kinase.

\* \* \* \* \*